United States Patent [19]
Gwaltney, Jr.

[11] Patent Number: 5,240,694
[45] Date of Patent: Aug. 31, 1993

[54] COMBINED ANTIVIRAL AND ANTIMEDIATOR TREATMENT OF COMMON COLDS

[75] Inventor: Jack M. Gwaltney, Jr., Free Union, Va.

[73] Assignees: University of Virginia, Charlottesville; Center for Innovative Technology, Herndon, both of Va.

[21] Appl. No.: 794,520

[22] Filed: Nov. 19, 1991

Related U.S. Application Data

[63] Continuation-in-part of Ser. No. 764,004, Sep. 23, 1991, abandoned.

[51] Int. Cl.$^5$ .................. A01N 25/34; A61K 9/14; A61K 9/48; A61L 9/04
[52] U.S. Cl. .................. 424/45; 424/405; 424/408; 424/434; 424/435; 424/451; 424/464; 424/489
[58] Field of Search .............. 424/408, 434, 435, 451, 424/464, 489, 405, 474, 45

[56] References Cited

U.S. PATENT DOCUMENTS 4,269,842  5/1991  Farge et al. .................. 514/291
5,137,876  9/1992  MacCoss et al. .................. 536/121

OTHER PUBLICATIONS

Gwaltney, "Combined Antiviral and Antimediator Treatment of Rhinovirus Colds", J. Infect. Dis, 166:776–82 (1992).
Hayden et al., J. Infect. Dis., 150:174–180 (1984).
Gaffey et al., Antimicrob. Agents Chemotherap., 32:1644–7 (1988).
Sperber et al., Annls. Int. Med., 117:37–41 (1992).

Primary Examiner—Thurman K. Page
Assistant Examiner—Carlos Azpuru
Attorney, Agent, or Firm—Whitham & Marhoefer

[57] ABSTRACT

The common cold is best treated by providing a combination of antiviral agents and antiinflammatory compounds to a patient infected with a cold virus. An antiviral agent and two antiinflammatory compounds given to a person infected with a cold virus simultaneously reduces the likelihood of a cold developing and the amount and duration of viral shedding, as well as substantially reduces the severity of individual cold symptoms and the overall number and severity of cold symptoms. Supplementing the activity of the combined antiviral and antiinflammatory agents with such compounds as antihistamines and alpha agonists results in suprisingly good nasal benefits. The combination therapy, termed COVAM therapy, is well tolerated and has no evidence of short-term toxicity.

11 Claims, 5 Drawing Sheets

Viral Shedding, Antibody Response, and Illness Occurrence in Rhinovirus Infected Subjects on Treatment or Placebo.

| Study | Group | No/Group | Virus Shedding (days) | No/Seroconv. | Final (GMT*) | Colds |
|---|---|---|---|---|---|---|
| 1 | Treatment | 6 | 3.2 ± 0.5 | 3 | 6.8 ± 3.6 | 2 |
|   | Placebo | 3 | 4.3 ± 0.3 | 2 | 16.0 ± 6.9 | 3 |
| 2 | Treatment | 11 | 2.6 ± 0.4 | 8 | 6.8 ± 1.1 | 5 |
|   | Placebo | 5 | 4.4 ± 0.4 | 4 | 6.4 ± 1.8 | 4 |
| Total | Treatment | 17 | 2.8 ± 0.3 | 11 (65%) | 6.8 ± 1.2 | 7 (41%) |
|   | Placebo | 8 | 4.4 ± 0.3+ | 6 (75%) | 8.8 ± 2.1 | 7 (88%) |

FIGURE 2

Total and Individual Symptom Scores in Rhinovirus Infected Subjects on Treatment or Placebo.

Mean Score/4 Days of Treatment

| Study | Group | Total | Sneeze | Rhinorrhea | Obstruction | Sore Throat | Cough | Headache | Malaise |
|---|---|---|---|---|---|---|---|---|---|
| 1 | Treatment | 9.0 ± 4.1 | 1.2 ± 0.6 | 1.2 ± 1.0 | 3.3 ± 1.1 | 2.0 ± 1.2 | 0.8 ± 0.7 | 0.3 ± 0.2 | 0.2 ± 0.2 |
|  | Placebo | 23.0 ± 3.7 | 1.3 ± 0.3 | 2.3 ± 0.3 | 6.0 ± 0.0 | 5.7 ± 0.9 | 3.7 ± 1.2 | 0.7 ± 0.7 | 3.0 ± 1.2 |
| 2 | Treatment | 9.6 ± 2.8 | 1.3 ± 0.6 | 1.4 ± 0.6 | 3.0 ± 1.0 | 1.5 ± 0.5 | 1.2 ± 0.6 | 0.5 ± 0.2 | 0.5 ± 0.3 |
|  | Placebo | 26.2 ± 4.0 | 1.4 ± 0.6 | 3.2 ± 1.1 | 5.8 ± 0.6 | 5.6 ± 1.3 | 2.0 ± 0.5 | 3.6 ± 1.5 | 4.0 ± 0.8 |
| Total | Treatment | 9.4 ± 2.2 | 1.2 ± 0.4 | 1.3 ± 0.5 | 3.1 ± 0.7 | 1.7 ± 0.5 | 1.1 ± 0.4 | 0.4 ± 0.2 | 0.4 ± 0.2 |
|  | Placebo | 24.9 ± 2.8 | 1.4 ± 0.4 | 2.9 ± 0.7 | 5.9 ± 0.4 | 5.6 ± 0.8 | 2.6 ± 0.6 | 2.5 ± 1.1 | 3.6 ± 0.6 |
|  | p = | <0.01 | >0.1 | 0.08 | <0.015 | <0.01 | 0.05 | 0.01 | <0.01 |

COMBINED ANTIVIRAL AND ANTIMEDIATOR TREATMENT OF COMMON COLDS

CROSS-REFERENCE TO RELATED PATENT APPLICATIONS

This patent application is a continuation-in-part (CIP) application of the co-pending patent application having the same title and inventor filed Sept. 23, 1991, which has Ser. No. 07/764,004, now abandoned and that patent application is herein incorporated by reference.

BACKGROUND OF THE INVENTION

1. Field of the Invention

The present invention generally relates to the treatment of the common cold and, more particularly, to a method and kit for cold treatment which employs both antiviral and antimediator agents.

2. Description of the Prior Art

The "common cold" is a time honored phrase used by both physicians and lay persons alike for the identification of acute minor respiratory illness. Since the discovery of rhinovirus in 1956, a considerable body of knowledge has been acquired on the etiology and epidemiology of common colds. It is known that the common cold is not a single entity, but rather is a group of diseases caused by members of several families of viruses including parainfluenza viruses, rhinoviruses, respiratory syncytial viruses, enteroviruses, and coronaviruses. Much work has been performed in characterizing viruses which cause the common cold. In addition, the molecular biology of rhinoviruses, the most important common cold viruses, is understood in great detail. In contrast, progress on the treatment of common colds has been slow despite these advances. While there is now a large number of compounds which have been found to exhibit antiviral activity against cold viruses in cell culture, antiviral compounds have had limited effectiveness in patients.

SUMMARY OF THE INVENTION

It is therefore an object of the invention to provide a method of treating the common cold which utilizes both antiviral and antiinflammatory compounds.

It is another object of the invention to provide a method of treating the common cold which employs the simultaneous administration of intranasal and oral medicants where the combination of medication provides both antiviral and antiinflammatory activity.

According to the invention, it was hypothesized that a major cause of common cold symptoms is host inflammatory responses to infection in addition to direct virus induced cytopathology. Experiments were conducted which showed that the simultaneous administration of antiviral and antiinflammatory compounds to patients suffering a rhinovirus induced cold had marketedly greater effect on treating the colds than the total cold combatting effects of each of the compounds taken separately. The treatment involved the use of both intranasal and oral medication. The treatment regimen is called "COVAM" therapy which is an acronym of combined virostatic (antiviral) antimediator therapy. Further experiments have shown that combining COVAM therapy with additional antimediators, such as by using alpha adrenergic agents and antihistamines in combination with the combined virostatic (antiviral) antimediator therapy, has dramatic benefits in a patient's subjective complaints related to rhinorrhea and on the measured weights of expelled nasal secretions.

BRIEF DESCRIPTION OF THE DRAWINGS

The foregoing and other objects, aspects and advantages will be better understood from the following detailed description of a preferred embodiment of the invention with reference to the drawings, in which:

FIG. 2 is a table showing the viral shedding, antibody response, and illness occurrence for placebo and treated groups in two different experiments and the combined results of the two experiments;

FIG. 3 is a table showing the total and individual symptom scores of rhinovirus infected subjects during two different experiments and the combined results of the two experiments;

DETAILED DESCRIPTION OF A PREFERRED EMBODIMENT OF THE INVENTION

Figure 1:
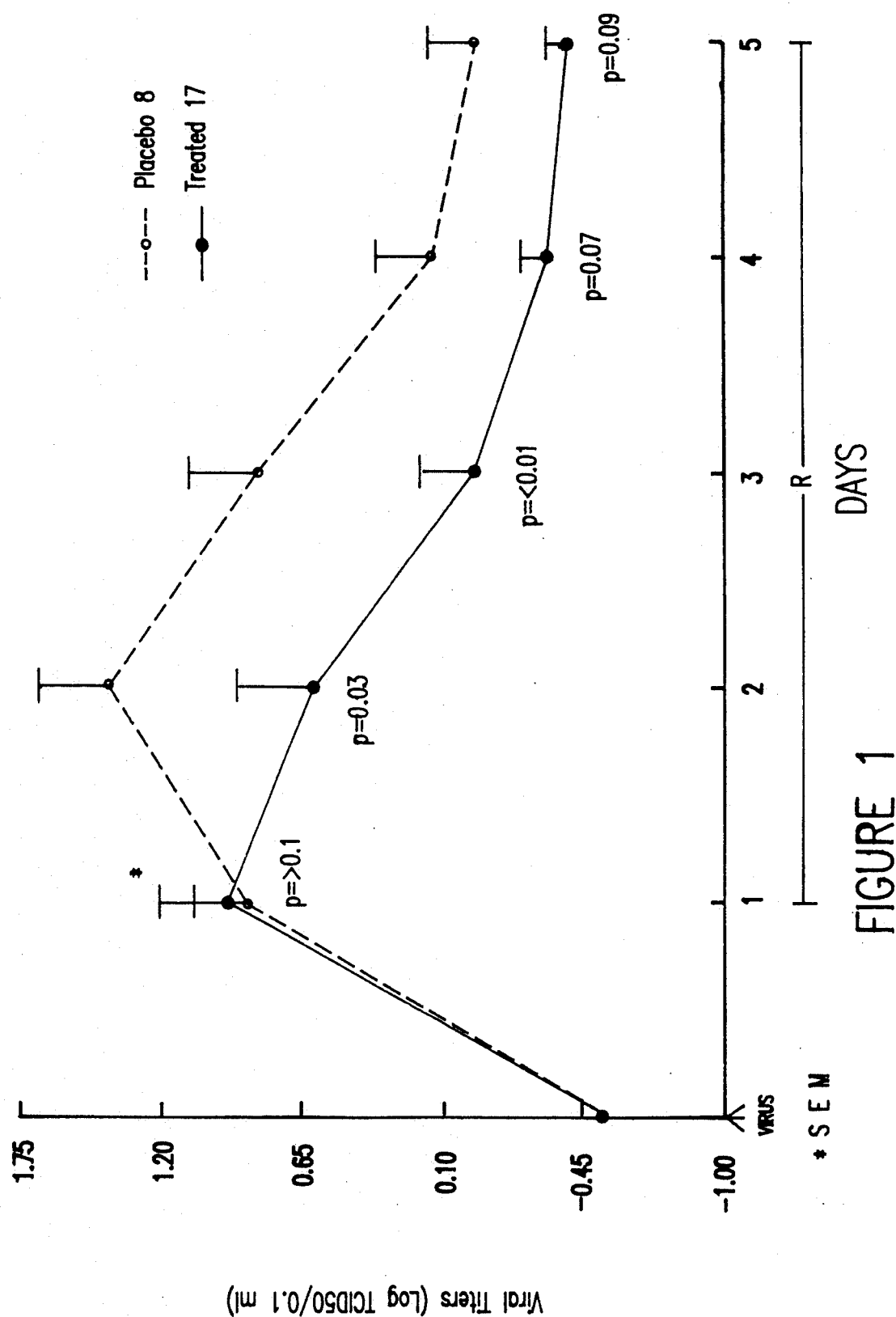
FIG. 1 is a graph showing the average measured viral titers for placebo and treated groups over a five day period of study.

Investigations with human subjects have been conducted for a new treatment for the common cold. In a first investigation, twenty eight healthy adult volunteers with serum neutralizing antibody titers of less then or equal to 1:2 to an unnumbered rhinovirus, Hank's strain, were recruited. As will be discussed below, the first investigation as conducted as two separate studies. In a second investigation, twenty subjects similar to those in the first investigation were used. In both investigations, each of the subjects gave a written consent in a form approved by the University of Virginia Human Investigation Committee. Subjects were excluded if they had a history of acute or chronic respiratory illness, a history of sinusitis, allergic rhinitis, asthma, nasal polyps, alcoholism, or drug abuse; had used nasal decongestants or antiinflammatory drugs within twenty four hours, antihistamines with seventy two hours, or monoamine oxidase inhibitors, phenothiazines, or topical or oral steroids within thirty days of initiation of the study. Persons with hypersensitivity to antiinflammatory drugs or severe drug allergy were also excluded, as were pregnant or lactating females. Only subjects who became infected with the challenge virus were included in the investigations.

In both investigations, the virus challenge was an intranasally administered Hank's strain of rhinovirus. The virus was provided as coarse drops in the form of two inocula (0.25 ml per nostril) given approximately ten minutes apart with the subject supine (laying down). Each subject was asked not to blow his/her nose for thirty minutes after the viral challenge. The viral inoculum contained a total of 30 $TCID_{50}$ per volunteer, where $TCID_{50}$ defines the tissue culture infection dose of virus capable of infecting 50% of culture tubes in which it is inoculated.

The compounds selected for COVAM therapy each have different mechanisms of action and each have shown therapeutic activity when tested individually in the rhinovirus challenge model. Commercially produced interferon α-2, available from the Schering Corporation, with pre-packaged diluent (bacteriostatic water) was prepared in vials daily. The dosage was three million units three times a day, given in coarse drops (0.1 ml per nostril). The diluent was used as the placebo in the first study of the first investigation and sterile physiologic saline was used as the placebo for the second study of the first investigation. Ipratropium, which is commercially available from Boehringer-Ingelheim Corporation, was provided in small pressurized canisters with attached adapters for intranasal administration and was given at a dose of 80 μg (two puffs per nostril) three times a day. The placebo groups in the two studies of the first investigation were given a nasal spray with inert propellants in similar canisters. Naproxen, commercially available from the Syntex Corporation, was given in a dosage of a 500 mg loading dose followed thereafter by 250 mg three times a day. Similar appearing capsules were administered to the placebo groups in the two studies of the first investigation. The presumed mechanisms of action of the components in the combined treatment (COVAM therapy) are as follows: interferon α2 is perceived to have its major action in preventing viral replication, ipratropium is an inhibitor of parasympathetic nerve pathways, and naproxen is a propionic acid inhibitor of cylcooxygenase which is believed to exert its major effect on prostaglandins.

In the second investigation, the same antiinflammatory and antiviral compounds were used (e.g., naproxen, ipratropium, and interferon α-2) in the same dosages described above; however, the COVAM therapy was supplemented with topical phenylephrine.HCl and chlorpheniramine. Phenylephrine.HCl is an alpha adrenergic agonist available from the Sterling Drug company of New York and was added to the partially diluted interferon α-2 (described above for first investigation) to give a final concentration of 0.25% phenylephrine. Testing of this combination of interferon and phenylephrine in cell culture showed no loss of rhinovirus inhibitory activity. Placebo nose drops were given as in the first investigation. Chlorpheniramine maleate is an antihistamine which is given orally in tablet form and is available from Richlyn laboratories of Philadelphia. In the second investigation, opaque capsules identical to those of naproxen which contained 4 mg chlorpheniramine maleate were administered with the naproxen. Subjects in the second investigation received two placebo capsules which were identical to the capsules containing the naproxen and chlorpheniramine.

In both investigations, all medications were started twenty four hours after virus inoculation and continued for a total of four days. Dosing was done at eight o'clock in the morning, four o'clock in the afternoon, and twelve midnight. Intranasal drops containing the interferon or interferon plus phenylephrine were given with the subjects supine, followed by oral administration of the naproxen or naproxen and chlorpheniramine maleate, and then an intranasal spray of ipratropium was given with the subjects sitting.

As pointed out above, the first investigation was conducted as two separate studies, and the cohorts of subjects in each study were treated the same. The subjects were isolated in individual hotel rooms beginning twelve hours after virus inoculation. The subjects were assigned to receive either treatment or placebo and were blinded to their treatment status, as was the observer recording all clinical information. Participants remained in the hotel until the fifth day after the virus challenge. Following completion of the first study with the first cohort of volunteers, sample sizes were calculated for studying the second cohort based on effect sizes observed with the first cohort. Power was calculated under the assumption that findings in the first cohort represented true effects and that testing of the second cohort would be conducted at the $\alpha = 0.05$ level of significance. A power of ninety percent for study days three and four was found to be obtainable with seven subjects per group. The data were initially analyzed independently by cohort and then combined for final analysis. Viral titers, duration of virus shedding, symptom scores, and mucus weights were analyzed using the t test. Data comparing proportion were analyzed by Fisher's exact test. All p-values are two tailed. Of the twenty eight subjects which were challenged with the virus, twenty five were "evaluable". One subject was excluded because he was infected with a wild strain of rhinovirus before viral challenge, and two subjects did not become infected with the challenge virus. Of the evaluable subjects, seventeen received treatment and eight received placebo. The mean age of persons receiving drug treatment was 21.1 years and persons receiving placebo was 22.1 years. Of the evaluable subjects, ten males and seven females received drug treatment, and five males and three females received placebo.

To monitor infection, nasal washes of each subject were collected prior to virus inoculation and once each morning. Washes were done by placing 5 ml of saline in each nostril. After a ten second count, secretions were expelled from both nostrils into a waxed paper container. After mixing in a syringe, portions of the nasal wash specimen were distributed for testing and the remainder stored frozen in plastic vials at $-70°$ C. Washings were cultured for rhinovirus on human embryo lung fibroblast cells (WI-38) according to the procedures described in Gwaltney et al., *J. Infect. Dis.*, 142:811–815 (1980), which is herein incorporated by reference. Three milliliters from each of the washes was pooled with one ml of viral collecting broth to prepare specimens for rhinovirus isolation and viral infectivity titers. One hundred-thirty microliters of antibody to interferon α2, which was purified by ammonium sulfate precipitation, was added to one ml of viral collecting broth and the mixture was added to all specimens from subjects which had received the treatment to neutralize residual interferon activity which would interfere with viral recovery.

FIGS. 1 and 2 present data obtained during the investigation which provide measures of infection for the cohorts of subjects in both studies. FIG. 1 presents the average measured viral titers of the treated and placebo groups on each of the five days after inoculation with the rhinovirus where the results of the cohorts of subjects for both of the studies in the investigation have been combined. Viral titers were determined by duplicate culture of serial tenfold dilutions of once frozen and thawed nasal wash specimens. Titers were calculated by the Karber method which is described in detail in Lennette et al., *Laboratory Diagnostics of Infectious Diseases*, NY: Springer-Verlag, 1988, p.51, and which is herein incorporated by reference. Samples that did not grow virus were assigned a value of 0.5 $\log_{10}$ $TCID_{50}$. FIG. 1 shows that for the groups receiving COVAM therapy, the peak viral titer occurred on the first day after viral challenge and thereafter declined. The trend corresponds with COVAM therapy beginning on the first day after inoculation. Conversely, the groups receiving placebo had a peak viral titer on the second day after viral challenge and the viral titers for the placebo groups were significantly higher in the placebo group on the second and third days than with the COVAM therapy treated groups. This indicates that COVAM therapy resulted in reduced viral replication relative to placebo, and that the natural history of the infectous process had been reversed.

In the investigations, infection was defined as recovery of the challenge virus from nasal washings on at least one day and/or a fourfold or greater rise in serum neutralizing antibody to Hank's strain rhinovirus. Isolates were identified as Hank's strain rhinovirus by neutralization with type-specific antibody. According to the procedures set forth in Gwaltney et al., *Rhinovirus*, Schmidt NJ, Emmons Rw eds. *Diagnostic Procedures for Viral Rickettsial and Chlamvdial Infections*, 6th ed., Wash. D.C.: American Public Health Association, 1989, p. 604., which is herein incorporated by reference, sera were obtained in screw capped tubes immediately prior to viral challenge and three weeks after inoculation for measuring homotypic antibody to Hank's strain rhinovirus.

FIG. 2 shows that virus was recovered from seventeen of the subjects in the groups receiving treatment and eight of subjects in the groups receiving placebo. As discussed above, the total number of subjects in the investigation was twenty eight. Of those, nineteen subjects received treatment, which corresponds to a eighty nine percent rate of infection in the treatment group, and nine subjects received placebo, which also corresponds to an eighty nine percent rate of infection in the placebo group. For the twenty five virus positive subjects, the mean duration of virus shedding, which is defined as the period during which virus was recovered by culture, was $4.4 \pm 0.3$ days for the placebo group and $2.8 \pm 0.3$ days for the treatment group ($p=0.003$). The shortened period of time for shedding the virus was statistically significant.

FIG. 2 also shows that fourfold or greater serum neutralizing antibody responses occurred in eleven of seventeen (sixty five percent) and six of eight (seventy five percent) of the subjects in the treatment and placebo groups, respectively. Post-infection geometric mean antibody titers were $6.8 \pm 4.8$ and $8.8 \pm 6.0$ in the treatment and placebo groups, respectively. The differences between the groups in the fraction who seroconverted or in their post-infection geometric mean titers were not statistically significant. This indicates that COVAM therapy had modest or no effect on the humoral immune response to rhinovirus infection.

FIGS. 2 and 3 show the number of colds and the occurrence and severity of symptoms, respectively, experienced by the subjects during the investigation according to a modified Jackson criteria (See, Jackson et al., Arch. Intern. Med.., 101:267-78 (1958), which is herein incorporated by reference, and Gwaltney et al, *J. Infect. Dis.*, 142:811-815 (1980)). In brief, the occurrence and severity of symptoms were determined before virus challenge (day 0) and on each morning before the subject received the combined drug treatment or the placebo on post-virus challenge days one through five by a study nurse who recorded the subject's assessment of the symptoms over the twenty four hour period on the following five-point scale: 0=absent, 1=mild, 2=moderate, 3=severe, 4=very severe. The symptoms assessed were runny nose, nasal stuffiness, sneezing, sore throat, cough, headache, malaise, and chilliness. The total symptoms score was determined by adding the symptoms during the five day period. The score for each individual symptom present before virus challenge (day 0) was subtracted from each of the daily scores for that symptom. Information was also recorded daily concerning the presence of any other symptoms possibly related to drug toxicity.

FIG. 2 shows that colds, as judged by the modified Jackson criteria, developed in seven of seventeen (forty one percent) of the subjects which received treatment, while colds developed in seven of eight (eighty eight percent) of the subjects in the placebo groups ($p=0.04$). Diagnosis of a cold depended on a total symptom score of six or more and either presence of rhinorrhea on three or more days or the subjective impression of having had a cold. FIG. 3 shows that the mean total symptom score over the four days of treatment was $9.4 \pm 2.2$ for the treated subjects compared to a mean total symptom score of $24.9 \pm 2.8$ for the subjects in the placebo groups ($p \leq 0.01$). In agreement with the viral titer data presented in FIG. 1, the daily mean total symptom score for the subjects in the treatment groups increased slightly for the first day of treatment (second day after inoculation), and thereafter declined over the next three days to near the pre-illness value. Conversely, in the placebo group, the daily mean total symptom score continued to rise, peaking on the second day of treatment (third day after inoculation). This beneficial effect was confirmed by generalized multivariate analysis of variance which showed a 59% reduction in the average area under the four-day symptom curve for the treated group compared to the placebo group ($p=0.004$).

Scores for the individual symptoms over the four days of treatment were reduced in the treatment groups for all symptoms except sneezing and chilliness (although chilliness occurred infrequently in both groups). The difference observed were significant for rhinorrhea ($p=0.08$), nasal obstruction ($p \leq 0.05$), sore throat ($p \leq 0.01$), cough ($p=0.05$), headache ($p=0.01$), and malaise ($p \leq 0.01$). Part of the nasal obstruction scores recorded may have resulted from the physical effects of repetitive intranasal spraying and dropping of medications. Also, sneezing frequently accompanied installation of the drug or placebo. Sneezing is a somewhat dramatic symptom, but it does not substantially add to the total symptom score of rhinovirus colds.

Figure 4:
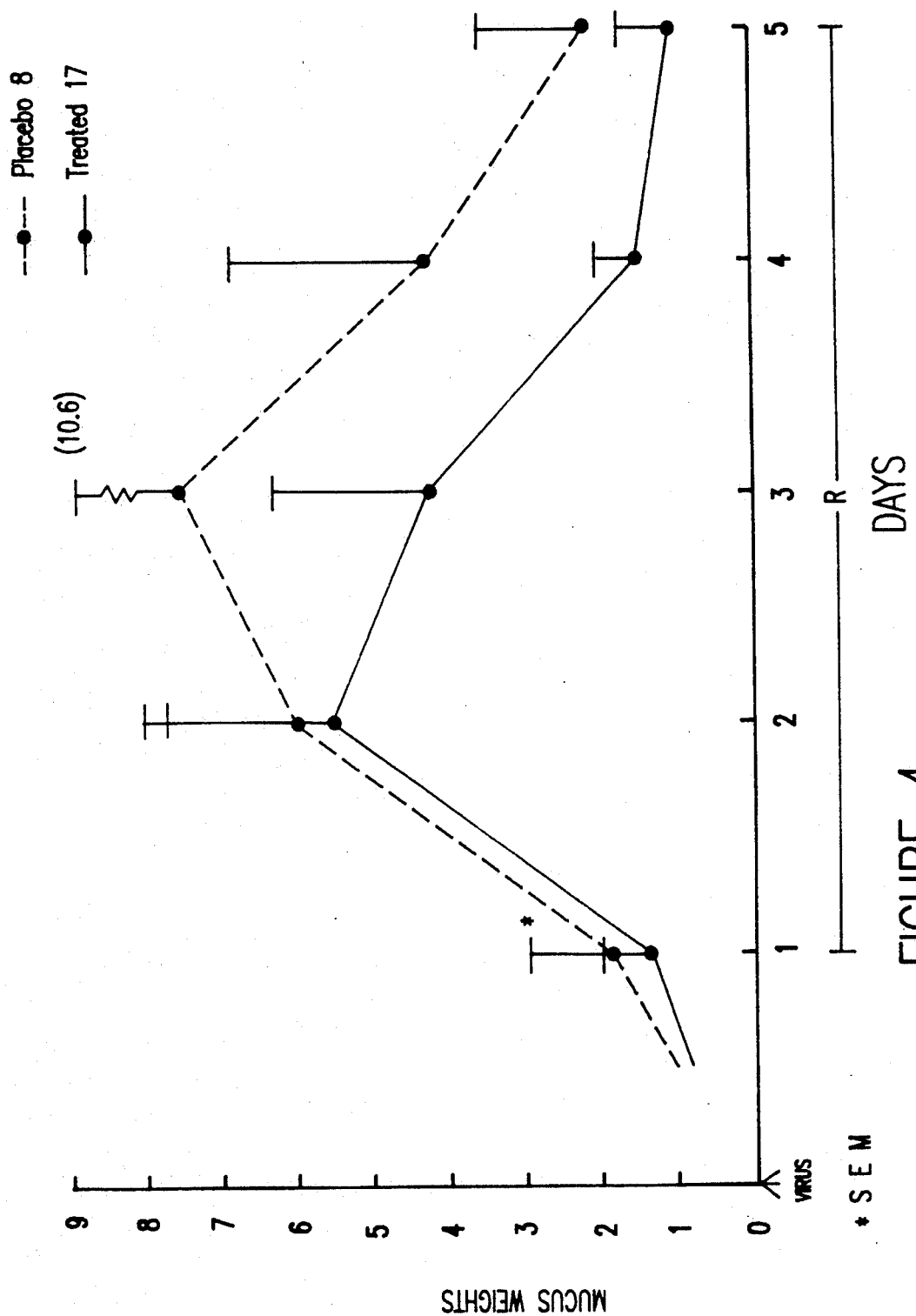
FIG. 4 is a graph showing the average measured mucus weights for treated and placebo groups over a five day period of study with COVAM therapy.

FIG. 4 shows the mucus weights (nasal secretions) for the treatment and placebo groups in both studies of the first investigation which were measured on a daily basis according to the method described in Doyle et al., *Pediatr. Infect. Dis. J.*, 7:215-242 (1988), which is herein incorporated by reference. Briefly, subjects collected used nasal tissues in air tight containers and the tissue collections were counted and weighed at 24 hour intervals with the weight of an equivalent number of unused tissues subtracted from that of the tissues used by the volunteers. The mean nasal mucous weights were only slightly lower in the treated group ($17.5 \pm 6.4$ gm/four days) than the placebo group ($20.3 \pm 5.4$ gm/four days) One individual in the treatment group produced a total of 91 gm of mucus, which may have skewed the results of the treatment group and placebo group closer together. The amount of mucus produced by this subject places him in the 98th percentile for nasal mucus production based on a review of 14 experiments involving 151 volunteers in Charlottesville using the rhinovirus challenge model. In retrospect, this subject also gave a history of having allergic rhinitis which he did not provide in the intake history. When the values of this subject were excluded from the analysis, the total mucus production over the four days for the treatment group declined by twenty seven percent to 12.9±4.8 gm/four days as shown in FIG. 4.

After the first investigation was completed, the subjects were asked to judge if they had been treated with the combination antiviral antimediator (COVAM) therapy or with placebo. Fourteen of the seventeen in the treatment group judged they had received drug COVAM, eight of which said cold symptoms started and then subsided, and four of which said that a cold never developed. Six out of eight subjects in the placebo group judged they were on placebo, two of which said that they had no relief from the symptoms In the group of seventeen subjects receiving treatment, there were four complaints of nasal stinging or burning, two complaints of nasal dryness, and one complaint each of mild epistaxis, muscle ache, "wakefulness", postnasal drip, and stomach cramps. In the group of eight subjects receiving placebo, there were three complaints of stuffy ear or earache, two complaints of nasal stinging or burning, and one complaint each of nasal dryness and chest congestion. All complaints were judged as mild and did not necessitate interruption of administration of the treatment or placebo.

The results of the first investigation show that by using a combination of an antiviral agent and two antiinflammatory compounds given simultaneously by the intranasal or oral route, it is possible to reduce the likelihood of a cold developing and the amount and duration of viral shedding, as well as substantially reduce the severity of individual cold symptoms and the overall number and severity of cold symptoms. The effectiveness of the COVAM therapy is believed to have resulted from the simultaneous inhibition of viral replication and the blocking of mediator activity due to virus already present in the nose at the time that treatment was started. Once COVAM therapy had had time to exert its full effect, there was less virus produced in the nasal cells and the mediator stimulating effect of virus which was produced was reduced or blocked. COVAM therapy was well tolerated and there was no evidence of short-term toxicity The second investigation was conducted to determine if any shortcomings of COVAM therapy, such as nasal symptoms or the like, could compensated for by supplementing the antiinflammatory and antiviral compounds (e.g., naproxen, ipratropium, and interferon) with an antihistamine or an alpha agonist. As discussed above, the alpha adrenergic agent phenylephrine and the antihistamine chlorpheniramine were administered with the naproxen, irpratropium and interferon in the second investigation.

The second investigation was conducted in substantially the same manner as the first. However, a nasal wash was performed prior to viral challenge but on no other days of the second investigation. Specimens for viral culture were performed by having the volunteers expel nasal secretions onto a plastic film as described in Naclerio et al., J. Infect. Dis., 157:133-42 (1988), which is herein incorporated by reference. This method was adopted to avoid possible irritation of the nasal passages by serial nasal washes. Twelve the twenty virus-challenged subjects in the second investigation were evaluable. Three subjects grew a wild strain of rhinovirus from the preinoculation culture, and the challenge virus was not recovered from five. The mean ages were 21.9 and 22.6 in the treated and placebo groups, respectively. Three males and four females received the supplemented COVAM therapy treatment and one male and four females received placebo. Colds occured in six of seven subjects in the treated group and in all five subjects of the placebo group. The mean (±SEM) total symptom score for the four days of treatment was 27.6 (±8.0) in the placebo group and 16.3 (±4.2) for the treated group (p=0.2 ). The mean (±SEM) four-day rhinorrhea score was 3.8 (±1.6) in the placebo group and 0.9 (±0.6) in the treated group (p=0.08). Trends associating COVAM therapy with benefits in headache, malaise, chilliness, and cough were seen as in the first investigation, but sneezing, nasal obstruction and sore throat scores were similar in the two groups. There was an increased incidence of sore throat in the treated group in the second investigation relative to the treated group in the first investigation; however, this may be due to the irritating effect of phenylephrine on the pharynx.

Figure 5:
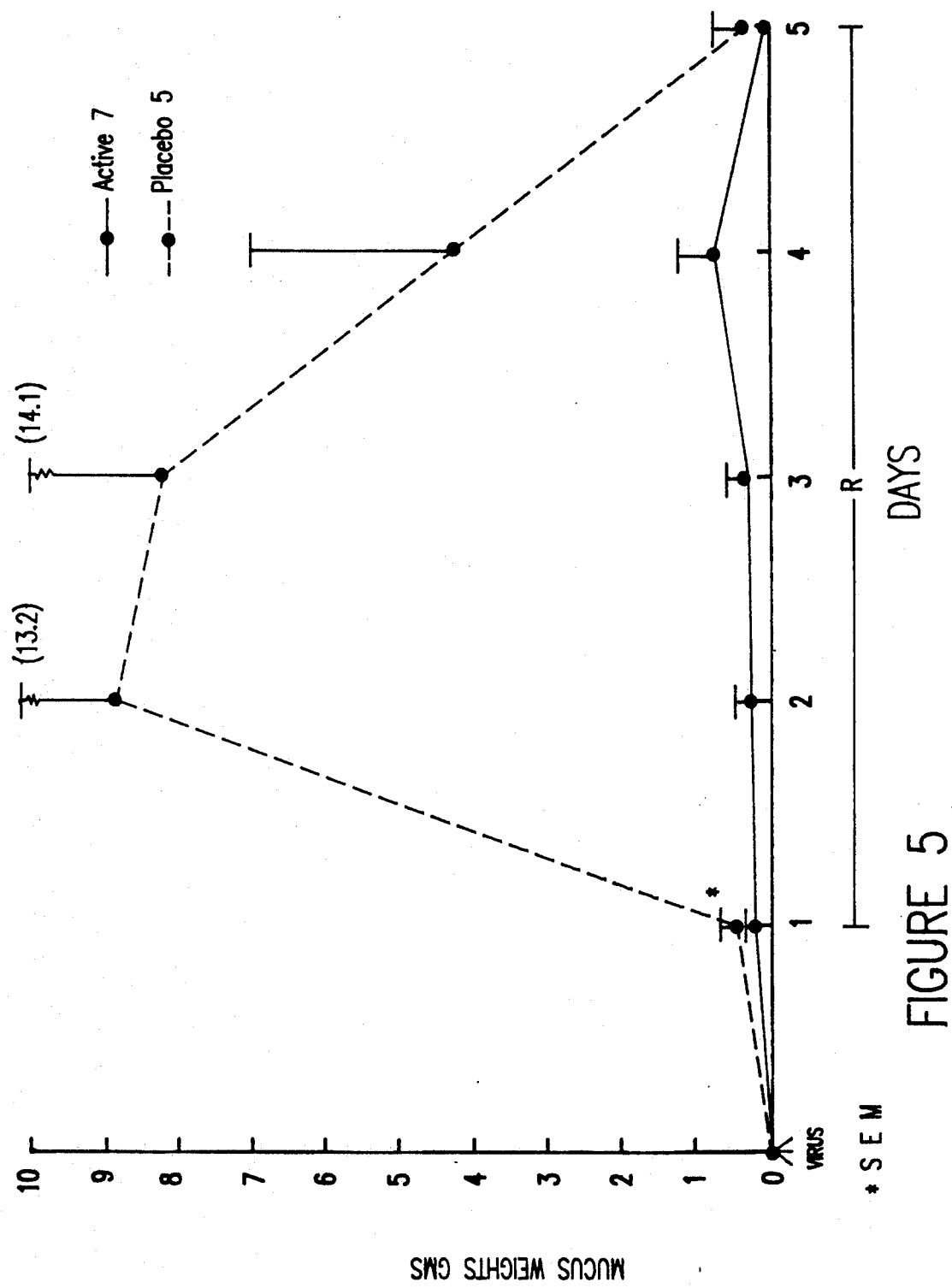
FIG. 5 is a graph showing the average measured mucus weights for treated and placebo groups over a five day period of study when COVAM therapy was supplemented with an alpha adrenergic agent and an antihistamine.

FIG. 5 shows that supplementing COVAM therapy with an alpha adrenergic agonist and an antihistamine had a marked effect on volume of nasal secretions produced. The mean (±SEM) four day total of nasal secretions was 22.2 (±12.9) gm for the five subjects in the placebo group and 1.6 (±0.6) gm for the seven subjects in the treated group (p=0.8); a remarkable 90% reduction.

Six of the seven subjects in the supplemented COVAM therapy treated group reported that cold symptoms were milder and did not develop as expected and three specifically mentioned the paucity of nasal secretions. Of the ten subjected receiving treatment, one reported drowsiness, one reported feeling tired, one reported burning in the nose, and one reported itching of the eyes. Of the ten subjects receiving placebo, two repored nasal burning, one nasal dryness, one nausea, and one drowsiness. The dramatic effects seen in the subjective complaints of rhinorrhea and on the measured weights of expelled nasal secretions may be due in part to the vasoconstrictive action of phenylephrine in reducing transudation of intravascular fluid in the nasal passages. Also, chlorpheniramine may have blocked some action or actions of histamine which play a role in stimulating the production of nasal secretions.

The rhinovirus challenge model used in this investigation has been used before to evaluate each of the individual components of the combined treatment taken alone. Specifically, Hayden et al., J. Infect. Dis., 150:174-80 (1984) describes the intranasal interferon α2 treatment of rhinovirus colds and Gaffey et al., Antimicrob. Aents Chemother., 32:1644-7 (1988) describes the ipratropium bromide treatment of experimental rhinovirus infection, and both of these articles are incorporated by reference. In addition, an article by Sperber et al., on which the inventor of this invention is noted as an author, has been submitted to Annls. Int. Med. and it describes the beneficial effects of naproxen in experimental rhinovirus colds. In the naproxen study of the submitted article, 39 patients received naproxen at a loading dose of either 400 or 500 mg. followed by either 200 or 500 mg of naproxen three times a day for five days where treatment began 6 hours after virus challenge. The experimental design was similar and the methods of evaluation and symptom scoring reported in each of the articles was identical to that used in the present investigation. In the ipratropium study, there was no difference in the mean total symptom scores during four days of treatment (ipratropium group 10±1.6; placebo/control group 9.5±1.2), although ipratropium had a mild beneficial effect on nasal symptoms and nasal mucus production. In the interferon study, the mean total symptoms score during four days of treatment (13.4±1.6) was slightly lower than the score for the placebo/control group (15.1±2.4), but the difference was not significant. Interferon treated subjects also had less nasal symptoms and nasal mucus production than controls. In the naproxen study, the mean total symptoms score for the naproxen group during the four days of treatment (12±1.65) was thirty four percent lower than that for the group receiving placebo (17.35±2.6)(p=0.08). In the naproxen study, headache, malais, myalgia, and cough were significantly reduced in the treated group.

Comparing these results with those obtained for COVAM therapy, the magnitude of improvement in the mean total symptom score for the group receiving the COVAM treatment (fifty nine percent for first investigation) was considerably greater than that seen when the results with individual treatments are combined, suggesting that the COVAM therapy had a syn-ergistic effect in reducing symptoms of experimental rhinovirus colds. As pointed out above, this improvement in effectiveness is believed to have resulted from the simultaneous inhibition of viral growth and the blocking of mediator activity which was occuring because of virus already present in the nose. Once COVAM therapy began to exert its full effect, there was less virus produced in the nasal cells and the mediator stimulating effect of any virus which was produced was reduced or blocked. The second investigation showed that supplementing COVAM therapy can have dramatic effects in terms of subjective complaints of rhinorrhea and nasal secretion production. The effectiveness of the COVAM therapy is also greater than that reported for a number of other treatments of experimental rhinovirus colds (See, Phillpotts et al., Lancet, 1:1342-44 (1981), Phillpotts et al., Antimicrob. Agents Chemother., 23:671-75 (1983), Al-Nakib et al., J. Antimicrob. Chemother., 20:893-901 (1987), Farr et al., Antimicrob. Agents Chemother., 31:1183-87 (1987), Al-Nakib et al., Antimicrob. Agents Chemother., 33:522-5 (1989), Hayden et al., Antiviral Res. 233-47 (1988), Gaffey et al., Amer. Rev. Respir. Dis., 136:556-60 (1987), Sperber et al., Bull NY Acad. Med., 65:145-60 (1989), and Farr et al., J. Infect. Dis., 162:1173-7 (1990)). The benefits of the COVAM therapy and supplemented COVAM therapy also appears to be superior to available commercial cold remedies based on the known mechanism of action of the ingredients in those remedies.

While the antiviral agent used in the investigations was inteferon $\alpha 2$, other antiviral agents which are specific for viruses commonly found in colds should yield the same synergistic cold combatting results when used in combination with antiinflammatory compounds. As suitable examples of antiviral agents that could be used in COVAM therapy, Sperber et al., Antimicrob. Agents Chemother., 32:409-419 (1988), which is herein incorporated by reference, provides a listing of representative antiviral agents with activity against rhinovirus which includes the following: Inteferons ($rIFN-\alpha_{2b}$, $rIFN-\alpha_{2a}$, $rIFN-\beta_{serine}$), Interferon inducers (Poly I:C, N,N-Dioactadecyl-N', N'-bis-(2-hydroxyethyl)-propanediamine (CP-20,961), Capsid binding agents/inhibitors of uncoating (4',6-Dichloroflavan (BW 683C), 4'-ethoxy-2'hydroxy-4,6'-dimethoxychalcone (Ro 09-0410), 5-ethoxy-3-methoxy-2-(p-methoxy-trans-cinnamoyl)-phenylphosphate (Ro 09-0415), 1-(5-tetradecyloxy-2-furanyl)ethanone (RMI 15,731), 2-[-(1,5,10,10a-tetrahydro-3H-thiazolo[3,4b]isoquinolin-3-ylindene)amino]-4-thiazole acetic acid (44,081 R.P.), Disoxaril, 5-[7-[4-(4,5 dihydro-2-oxazolyl)phenoxy]heptyl]-3-methylisoxazole (WIN 51,711), 3-methoxy-6-[4-(3-methylphenyl)-piperazinly]pyradazine (R61837), 3,4-dihydro-2-phenyl-2H-pyrano[2,3-b]pyridines, and phenoxypyridinecarbonitriles), 2-(3,4-dichlorophenoxy)-5-nitrobenzonitrile (MDL 860), Benzoimidazoles (Enviroxime, 2-amino-1-(isopropyl sulfonyl)-6-benzimidazole phenyl ketone oxime), 1'-methyl spiro(adamantane-2,3-pyrrolidine)maleate, Isatin thiosemicarbazone, Fusidic acid, Substituted trizainoindoles (4-([8-amino-7-chloro-5-methyl-5H-as-triazino(5,6-b)indol-3-yl]amino)-2-methyl-2-butanol (SK&F 40491)), 2,6-diphenyl-3-methyl-2,3-dihydroimidazo[2,1-b]thiazole (RP 19236), 3-alpha-naphthl-5-diethylcarbamoyl-1,2,4,-oxadiazole (GL R9-338), Oxolinic acid, Isoquinolines (1-(p-chlorophenoxymethyl)-3,4-dihydroisoquinone hydrochloride (UK-2054), 3,4-dihydro-1-isoquinolineacetamide hydrochloride), 1-p-chlorophenyl-3-(m-3-isobutyl-guanidinophenyl)urea hydrochloride (ICI 73,602), and Zinc salts. Substances which prevent attachment of the rhinovirus to the nasal cells, such as anti ICAM-1 antibody [Hayden et al, Antiviral Res., 9:233-247 (1988)] and synthetic ICAM-1 [Greve et al., Cell, 56:839-847 (1989)], and other types of interferon should also be useful in COVAM therapy. In addition, agents which are known to be effective against influenza virus, another respiratory virus, such as amantadine, rimantadine, and ribavirin will be useful in COVAM therapy, as well as, antiviral agents which may become available to treat other cold viruses including coronavirus, parainfluenza virus, rhinovirus, adenovirus, influenza virus, and respiratory syncytial virus.

While the antiinflammatory compounds used in the investigations were ipratropium, naproxen, phenylephrine, and chlorpheniramine, other antiinflammatory compounds could be substituted or added within the practice of the invention. For example, it has been found that blocking cold symptoms can be accomplished by administering compounds which have their pharmacologic activity from blocking or inhibiting specific pathways of inflamamation. Specifically, this has been shown with atropine methonitrate [See, Gaffey et al., Amer. Rev. Respir. Dis., 135:241-244 (1987)] and ipratropium [See, Gaffey et al., Antimicrob. Agents Chemother., 32:1644-1647 (1988)] for the parasympathetic pathways of inflammation, with intranasal and systemic glucocorticoid steriods [See, Farr et al., J. Infect. Dis., 162:1173-1177 (1990)] for arachidonic acid metabolites, and with chlorpheniramine [See, Doyle et al., Pediatr. Infect. Dis. J., 7:229-238 (1988)] for histamine. All of the above compounds, as well as others which block, antagonize, or otherwise inhibit pathways of inflammation associated with the various signs and symptoms of acute respiratory disease would be expected to perform well in COVAM therapy.

Because the human immune system appears to have considerable redundancy in the pathways and mechanisms which are capable of stimulating inflammation, it is believed to be necessary to block multiple pathways in order to maximize the clinical effectiveness of the COVAM treatment. In the nose, there is evidence that at least seven pathways have a role in the production of signs and symptoms of illness during rhinovirus infection or natural colds. These pathways and mechanisms include the parasympathetic nevous systems [See, Gaffey et al., *Amer. Rev. Respir. Dis.*, 135:241-244 (1987) and Gaffey et al., Antimiro. Agents Chemother., 32:1644-1647 (1988)], the kinin (bradykinin and lysylbradykinin) pathway [See, Naclerio et al., *J. Infect. Dis.*, 161:120-123 (1990) and Proud et al., *J. Infect. Dis.*, 7:229-238 (1988)], the histamine pathway [See, Doyle et al., Pediatr. Infect. Dis. J., 7:229-238 (1988)], the interleukin-1 pathway [personal communication, Gwaltney], the alpha adrenergic pathway as shown by long established effectiveness of alpha adrenergic agonists (phenylepherine and pseudoephedrine), the metabolites of the cyclooxygenase pathway (the prostaglandins, etc.)[See, Farr et al., J. Infect. Dis., 162:1173-1177 (1990) as well as the Sperber et al. experiments with naproxen discussed above], and the exogenous opioid agonists [See, Diehl, J. Amer. Med. Assoc., 101:2042-2049 (1933)]. Other nonsteroidal antiinflammatory agents like naproxen, such as ibuprophen, should also be useful in COVAM therapy. In addition, there are other related and unrelated mechanisms of inflammation production which have not been investigated for colds, but which may also play a role in their pathogenesis including the metabolites of the lipoxygenase pathway (leukotrienes, etc.), the other interleukins, and the processes controlling intracellular calcium fluxes which are inhibited by the calcium channel blockers.

While the alpha agonist used in the second investigation was phenylephrine, other agonists could be substituted or added within the practice of the invention. For example, pseudoephedrine, phenylpropanolamine, oxymetazoline, and xylometazoline are exemplary compounds.

While the antihistamine used in the second investigation was chlorpheniramine, other agonists could be substituted or added within the practice of the invention. For example, diphenylhydramine, brompheniramine, clemastine, and terfenadine are exemplary compounds.

The total dosage used of the antiinflammatory and antiviral compounds in the first and second investigations were as follows: ipratropium=960 $\mu$g, interferon $\alpha 2 = 36$ million units, and naproxen $=3.25$ gm. The total dosage used of the supplementing compounds in the second investigation were as follows: phenylephrine=0.25% three times a day for four days, and chlorpheniramine $=48$ mg. The doses of compounds used in the investigations described were standard for adults with the exception of interferon $\alpha 2$, for which an optimal dose for treatment of colds has not been determined. Smaller doses may be possible while still retaining a satisfactory level of effectiveness. Dose levels for children would need adjustment to provide equivalence in effectiveness and safety to that of adult doses.

To provide ease of use for the patient and to optimize compliance, medications may be provided in a prepackaged kit containing both antiviral agents and antiinflammatory agents. The kit may contain a spray or dropper device for intranasal delivery of metered doses of combined medications for intranasal use and a blister pack containing premeasured doses of pills, capsules, caplets, etc., containing combined oral medications. Oral medications may also be given in combination with pharmacological binders, syrups, elixirs, and the like.

It is contemplated that a particularly good way of administering the drugs required for COVAM therapy or supplemented COVAM therapy simultaneously would be to package appropriate quantities of each in a metered dose inhaler (MDI) such that they may be delivered as an aerosol for inhalation. MDIs have become a well accepted method of delivering bronchodilators ($B_2$ agonists and anticholinergics), corticosteroids, and anti-allergics, and it is envisioned that inhalation would also be a viable means of delivering the types of compounds described above. MDIs comprise a pressure resistant container typically filled with a product such as a drug dissolved in a liquified propellant or micronized particles suspended in a liquified propellant where the container is fitted with a metering valve. Actuation of the metering valve allows a small portion of the spray product to be released whereby the pressure of the liquified propellant carries the dissolved or micronized drug particles out of the container to the patient. The valve actuator is used to direct the aerosol spray into the patient's airway (upper and lower). Surfactants are usually dissolved in the spray product and can serve the dual functions of lubricating the valve and reducing aggregation of micronized particles. Commonly used surfactants include oleic acid and sorbitan trioleate. The envisioned MDI could employ the commonly used chlorofluorocarbons (CFCs) such as $CCl_3F$ (Freon 11 or CFC-11), $CCl_2F_2$ (Freon 12 or CFC-12), and $CClF_2-CClF_2$ (Freon 114 or CFC-114), or some combination thereof, as the propellant. Alternatively, non-ozone depleting propellants such as hydrocarbons (propane, butane, etc.), dimethyl ether, carbon dioxide, 1,1,1,2-tetrafluoroethane (HFC-134a), and combinations thereof, or limited ozone depleting propellants such as HCFCs, and combinations thereof, could be employed as the propellant.

While the invention has been described in terms of its preferred embodiments, those skilled in the art will recognize that the invention can be practiced with considerable modification within the spirit and scope of the appended claims.

Having thus described my invention, what I claim as new and desire to secure by Letters Patent is as follows:

1. A method of treating the common cold, comprising the steps of:

administering to a patient in need thereof a therapeutically effective amount of at least one antiviral agent specific for a virus which causes the common cold selected from the group consisting of rhinoviruses, adenoviruses, enteroviruses, coronaviruses, respiratory synctial viruses, influenza viruses and parainfluenza viruses; and administering to said patient a therapeutically effective amount of at least one antiinflammatory compound specific for inflammatory pathways of the common cold selected from the group consisting of the parasympathetic pathway, the cyclooxygenase and lipoxygenase pathway, the histamine pathway, the alpha adrenergic pathway, the interleukin-1 pathway, the kinin pathway, and the pathway used by exogenous opioid agonists, said steps of administering said antiviral agent and said antiinflammatory compound being performed at approximately the same time and achieving a synergistic result in the treatment of the common cold.

2. A method as recited in claim 1 wherein said antinflammatory compound is selected from the group consisting of ipratropium, atropine methonitrate, exogenous opioid agonists, alpha adrenergic agonists, chlorpheniramine, prostaglandin blockers and antagonists, leukotriene blockers and antagonists, parasympathetic blockers and antagonists, interleukin blockers and antagonists, naproxen and ibuprophen.

3. A method as recited in claim 1 wherein said antiviral agent is selected from the group consisting of integerons, interferon inducers, capsid binding agents, benzoimidazoles, 1'-methyl spiro(adamantane-2,3-pyrrolidine)maleate, isatin thiosemicarbazone, fusidic acid, substituted trizainoindoles, 2,6-diphenyl-3-methyl-2,3-dihydroimidazo[2,1-b]thiazole, 3-alpha-naphthl-5-diethylcarbamoyl-1,2,4-oxadiazole, oxolinic acid, isoquinolines, 1-p-chlorophenyl-3-(m-3-isobutylguanidinophenyl)urea hydrochloride, anti ICAM-1 antibody synthetic ICAM-1, amantadine, rimantadine, and ribavirin.

4. A method as recited in claim 1 further comprising the step of administering to said patient a therapeutically effective amount of at least one antihistamine compound which is different from said antiinflammatory compound.

5. A method as recited in claim 4 wherein said antihistamine compound is selected from the group consisting of chlorpheniramine, diphenylhydramine, brompheniramine, clemastine, and terfenadine.

6. A method as recited in claim 1 further comprising the step of administering to said patient a therapeutically effective amount of at least one alpha agonist compound which is different from said antiinflammatory compound.

7. A method as recited in claim 6 wherein said alpha agonist is selected from the group consisting of phenylephrine, pseudoephedrine, phenylpropanolamine, oxymetazoline, and xylometazoline.

8. A method of treating the common cold, comprising the steps of:
administering to a patient in need thereof a therapeutically effective amount of at least one antiviral agent specific for a virus which causes the common cold selected from the group consisting of rhinoviruses, adenoviruses, enteroviruses, coronaviruses, respiratory syncytial viruses, influenza viruses and parainfluenza viruses; and
administering to said patient a therapeutically effective amount of at least two antiinflammatory compounds specific for at least two different inflammatory pathways of the common cold selected from the group consisting of the parasympathetic pathway, the cyclooxygenase and lipoxygenase pathway, the histamine pathway, the alpha adrenergic pathway, the interleukin-1 pathway, the kinin pathway, and the pathway used by exogenous opioid agonists, said steps of administering said antiviral agent and said two antiinflammatory compounds being performed at approximately the same time and achieving a synergistic result in the treatment of the common cold.

9. A method as recited in claim 8 wherein said antiviral agent is interferon $\alpha 2$, and wherein said antiinflammatory agents naproxen and ipratropium.

10. A method as recited in claim 8 wherein at least one of said antiviral agent and said antiinflammatory compounds is administered orally and at least one of said antiviral agent and said antiinflammatory compounds is administered nasally.

11. A method as recited in claim 8 wherein said antiviral agent and said antiinflammatory agents are administered simultaneously using a metered dose inhaler.

* * * * *